(12) United States Patent
Yu (10) Patent No.: US 12,151,037 B2
(45) Date of Patent: Nov. 26, 2024

(54) ULTRAVIOLET STERILIZATION DISPLAY DEVICE AND CONTROL METHOD THEREOF

(71) Applicant: AmTRAN Technology Co., Ltd., New Taipei (TW)

(72) Inventor: Hung-Ta Yu, New Taipei (TW)

(73) Assignee: AmTRAN Technology Co., Ltd., New Taipei (TW)

( * ) Notice: Subject to any disclaimer, the term of this patent is extended or adjusted under 35 U.S.C. 154(b) by 700 days.

(21) Appl. No.: 17/083,273

(22) Filed: Oct. 28, 2020

(65) Prior Publication Data

US 2021/0338859 A1   Nov. 4, 2021

(30) Foreign Application Priority Data

Apr. 30, 2020   (TW) ................... 109114630

(51) Int. Cl.
*A61L 2/10*   (2006.01)

(52) U.S. Cl.
CPC ............. *A61L 2/10* (2013.01); *A61L 2202/11* (2013.01); *A61L 2202/14* (2013.01)

(58) Field of Classification Search
CPC ...................................................... A61L 2/10
See application file for complete search history.

(56) References Cited

U.S. PATENT DOCUMENTS

| 9,492,576 B1 | 11/2016 | Cudak et al. |
| 9,669,121 B2 | 6/2017 | Liao et al. |
| 2015/0022730 A1 * | 1/2015 | Chang ................ G02F 1/13338 349/12 |
| 2021/0196848 A1 * | 7/2021 | Baarman ................ H04M 1/18 |

FOREIGN PATENT DOCUMENTS

| CN | 102284139 A |  | 12/2011 |  |
| CN | 104281292 A |  | 1/2015 |  |
| CN | 104297973 A |  | 1/2015 |  |
| CN | 104766546 A |  | 7/2015 |  |
| CN | 104822395 A |  | 8/2015 |  |
| CN | 110045545 A |  | 7/2019 |  |
| GB | 2565638 A | * | 2/2019 | ............. A61L 2/088 |
| KR | 20180016003 A | * | 12/2017 | ............... A61L 2/10 |
| KR | 101813077 B1 | * | 2/2018 | ............... A61L 2/10 |

(Continued)

OTHER PUBLICATIONS

Debasmita Patra, titanium dioxide, Mar. 27, 2023 Britannica (Year: 2023).*

(Continued)

*Primary Examiner* — Kevin Joyner
(74) *Attorney, Agent, or Firm* — CKC & Partners Co., LLC (57) ABSTRACT

An ultraviolet sterilization display device includes a sterilization panel, a titanium dioxide thin film, and a light emitting diode module. The sterilization panel includes an inner surface, an outer surface and a light incident surface. The titanium dioxide thin film is formed on the inner surface of the sterilization panel. The light emitting diode module is aligned with the light incident surface of the sterilization panel, and the light emitting diode module includes a plurality of ultraviolet light emitting diodes. In addition, a sterilization process of an ultraviolet sterilization display device is also disclosed herein.

15 Claims, 5 Drawing Sheets

(56) References Cited

FOREIGN PATENT DOCUMENTS

| | | |
|---|---|---|
| TW | M351363 U | 2/2009 |
| TW | M478860 U | 5/2014 |
| TW | 201504719 A | 2/2015 |
| WO | 2013141571 A1 | 9/2013 |

OTHER PUBLICATIONS

SpecialChem, Comprehensive List of Transparent Polymers, Oct. 25, 2017, Omnexus (Year: 2017).*
KR 101813077 B1_Translation.*
KR 20180016003 A_Translation.*

* cited by examiner

ULTRAVIOLET STERILIZATION DISPLAY DEVICE AND CONTROL METHOD THEREOF

RELATED APPLICATIONS

This application claims priority to Taiwan Application Serial Number 109114630, filed Apr. 30, 2020, which is herein incorporated by reference.

TECHNICAL FIELD

The present disclosure generally relates to a sterilization display device and control method thereof. More particularly, the present disclosure relates to an ultraviolet sterilization display device and control method thereof.

BACKGROUND

With the widespread use of flat panel displays in recent years, the flat panel displays with touch-control functions have been widely used in various electronic products. Regardless of the touch-control module is infrared scanning type, resistive type or capacitive type, users must touch the flat panel displays having touch-control modules with their fingers. For the large public information displays (PID) or the commercial flat-panel displays, the touch-control surfaces of the glass panels are often touched by many users. In the situation that multiple users have used a touch-control display, pathogens spread by contact will remain on the touch-control surface, so the next user may contact the pathogens, such as bacteria, viruses, fungi or parasites, when the next user uses the touch-control surface.

A current common disinfection or sterilization method is spraying ethyl alcohol or sterilization sprays on the touch area on the touch-control module of the flat panel display device. However, the large display devices generally incorporate infrared sensors and infrared light-emitting diodes to detect the user's touch activities. If the ethyl alcohol or sterilization sprays are accidentally sprayed on the infrared light-emitting diodes, the ethyl alcohol may cause the silver stents of the infrared light-emitting diodes being oxidized and deteriorated, which may cause damages to the detectors.

In addition, the traditional alcohol disinfection method cannot immediately eliminate the virus and prevent the spread. Generally, alcohol disinfection is performed manually at regular intervals, for example, spray ethyl alcohol or sterilization sprays every few hours on the objects. Therefore, if the touch-control displays are already used by users after a sterilization process, the users use the touch-control displays at the time period between previous users and the next sterilization process may also be exposed to the pathogens left by the previous users, and thus become a way for the transmission of the pathogen.

SUMMARY

One objective of the embodiments of the present invention is to provide an ultraviolet sterilization display device able to improve the quality and efficiency of sterilizing display device to avoid the spread of disease.

To achieve these and other advantages and in accordance with the objective of the embodiments of the present invention, as the embodiment broadly describes herein, the embodiments of the present invention provides an ultraviolet sterilization display device including a sterilization panel, a titanium dioxide thin film, a light emitting diode module and a display panel. The sterilization panel has an inner surface, an outer surface and a light incident surface. The titanium dioxide thin film is adhered to the inner surface of the sterilization panel. The light emitting diode module is aligning with the light incident surface of the sterilization panel, in which the light emitting diode module includes a plurality of ultraviolet (UV) light emitting diodes. The display panel is adjacent to the inner surface of the sterilization panel.

In some embodiments, the sterilization panel further includes an end surface opposite to the light incident surface, and two side surfaces connected to the light incident surface and the end surface, and the end surface and the side surfaces includes a reflecting layer.

In some embodiments, the reflecting layer includes a white reflecting surface or a silver reflecting surface.

In some embodiments, the sterilization panel is a light guide plate formed by a UV resistant material having a Non-UV light transmittance greater than 80%.

In some embodiments, the light emitting diode module further includes a circuit board fixing the ultraviolet light emitting diodes, a plurality of infrared (IR) light emitting diodes fixed on the circuit board, and a plurality of light detectors detecting lights emitted by the IR light emitting diodes.

In some embodiments, the ultraviolet sterilization display device further includes a proximity sensor to detect an object close to the sterilization panel.

According to another aspect of the present application, an sterilization process of an ultraviolet sterilization display device is provided, the ultraviolet sterilization display device includes a sterilization panel, an ultraviolet light emitting diode aligning with a light incident surface of the sterilization panel and a control chip electrically connected to the ultraviolet light emitting diode, and the sterilization process includes detecting whether an object is close to the sterilization panel or contacting the sterilization panel by a proximity sensor, storing detection records of the proximity sensor in a memory component, generating a signal by the control chip to activate the ultraviolet light emitting diode to emit ultraviolet lights for a period of time when the ultraviolet sterilization display device is in a shutdown state or a standby state and the stored detection records include that the object was detected as close to the sterilization panel or contacting the sterilization panel, and resetting the stored detection records in the memory component after the ultraviolet light emitting diode is driven to emit ultraviolet lights for the period of time, wherein a titanium dioxide thin film is disposed or formed on an inner surface of the sterilization panel.

In some embodiments, the stored detection records include a number of times and duration of the object close to the sterilization panel.

In some embodiments, the step of generating a signal by the control chip to activate the ultraviolet light emitting diode is determined by the control chip according to the number of times and duration of the object close to the sterilization panel.

In some embodiments, the sterilization process further includes turning off the ultraviolet light emitting diode by the control chip when the proximity sensor detects an object is close to the sterilization panel.

According to further another aspect of the present application, an sterilization process of of a touch-control display device is provided, the touch-control display device includes a sterilization panel, an ultraviolet light emitting diode aligning with a light incident surface of the sterilization panel and a control chip electrically connected to the ultraviolet light emitting diode, and the sterilization process includes automatically initiating the sterilization process when the touch-control display device is not operated for a predetermined time period, or when the touch-control display device is in a standby state or a shutdown state, wherein a titanium dioxide thin film is disposed or formed on an inner surface of the sterilization panel.

In some embodiments, the sterilization process further includes notifying not to operate the touch-control display device by displaying a warning picture, turning on an indicator light, playing warning sound, or starting vibration of the touch-control display device when the touch-control display device is going to initiate the sterilization process or is executing the sterilization process.

In some embodiments, the sterilization process further includes initiating the sterilization process when the touch-control display device is not operated and an ambient light sensor on a side surface of the touch-control display device detects that ambient light brightness is lower than a predetermined brightness value for a period of time.

In some embodiments, the sterilization process further includes detecting whether an object is contacting the sterilization panel, storing detection record in a memory component, and generating a signal by the control chip to activate the ultraviolet light emitting diode to emit ultraviolet lights for a period of time when the touch-control display device is in the shutdown state or the standby state and the stored detection records include that the object was detected as close to the sterilization panel or contacting the sterilization panel.

Hence, most of the ultraviolet light of the ultraviolet sterilization display device disclosed by the present invention will be totally reflected in the glass panel, and emit out of the glass panel from the outer surface of the non-titanium dioxide coated surface to sterilize pathogens such as bacteria and viruses on the outer surface of the glass panel. In addition, because the UV-C ultraviolet light is short-wavelength light, the transmission distance of UV-C ultraviolet light is quite short, which will not cause damage to objects such as human bodies at certain distance. Furthermore, when the IR light emitting diode and light detector are disposed to detect that the user touches the outer surface of the glass panel, the ultraviolet sterilization display device cuts off the current of the UV light emitting diode, thereby effectively improving the safety of the UV sterilization display device during use.

BRIEF DESCRIPTION OF THE DRAWINGS

The foregoing aspects and many of the attendant advantages of this invention will be more readily appreciated as the same becomes better understood by reference to the following detailed description, when taken in conjunction with the accompanying drawings, wherein.

DETAILED DESCRIPTION OF THE PREFERRED EMBODIMENT

The following description is of the best presently contemplated mode of carrying out the present disclosure. This description is not to be taken in a limiting sense but is made merely for the purpose of describing the general principles of the invention. The scope of the invention should be determined by referencing the appended claims.

Figure 1:
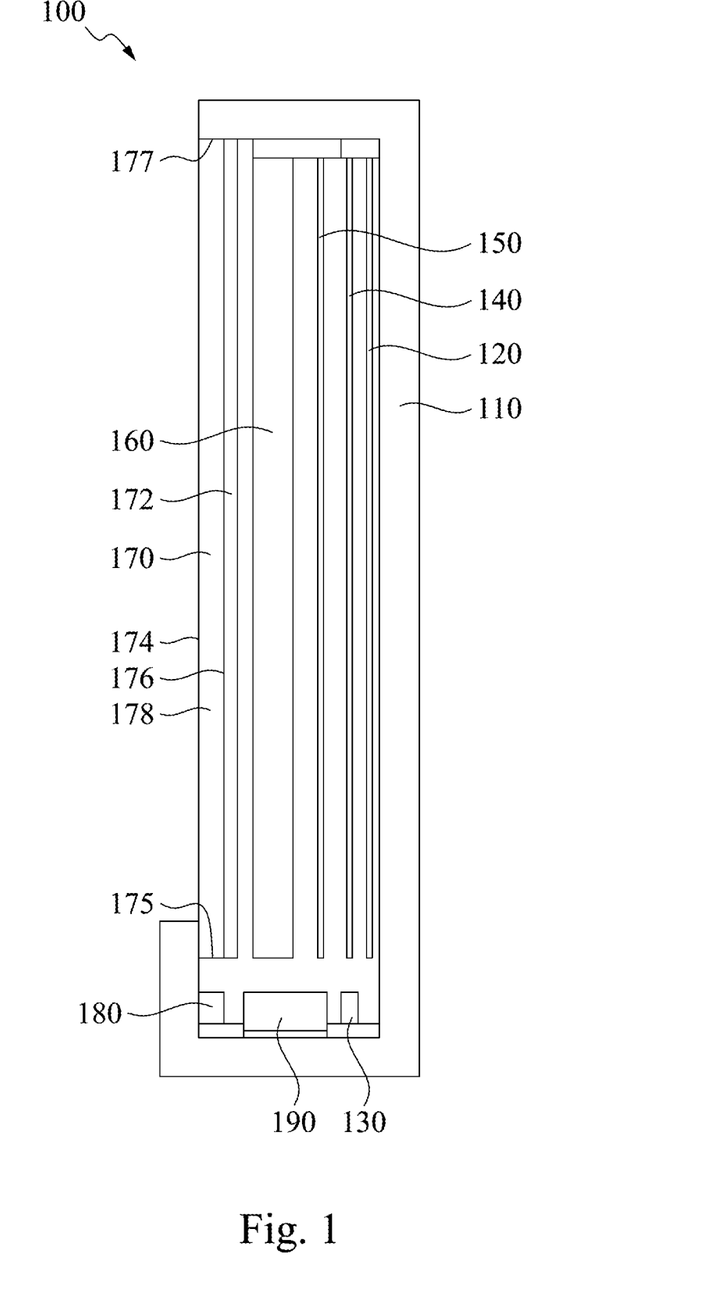
FIG. 1 illustrates a schematic diagram showing an ultraviolet sterilization display device according to one embodiment of the present invention.
Figure 2:
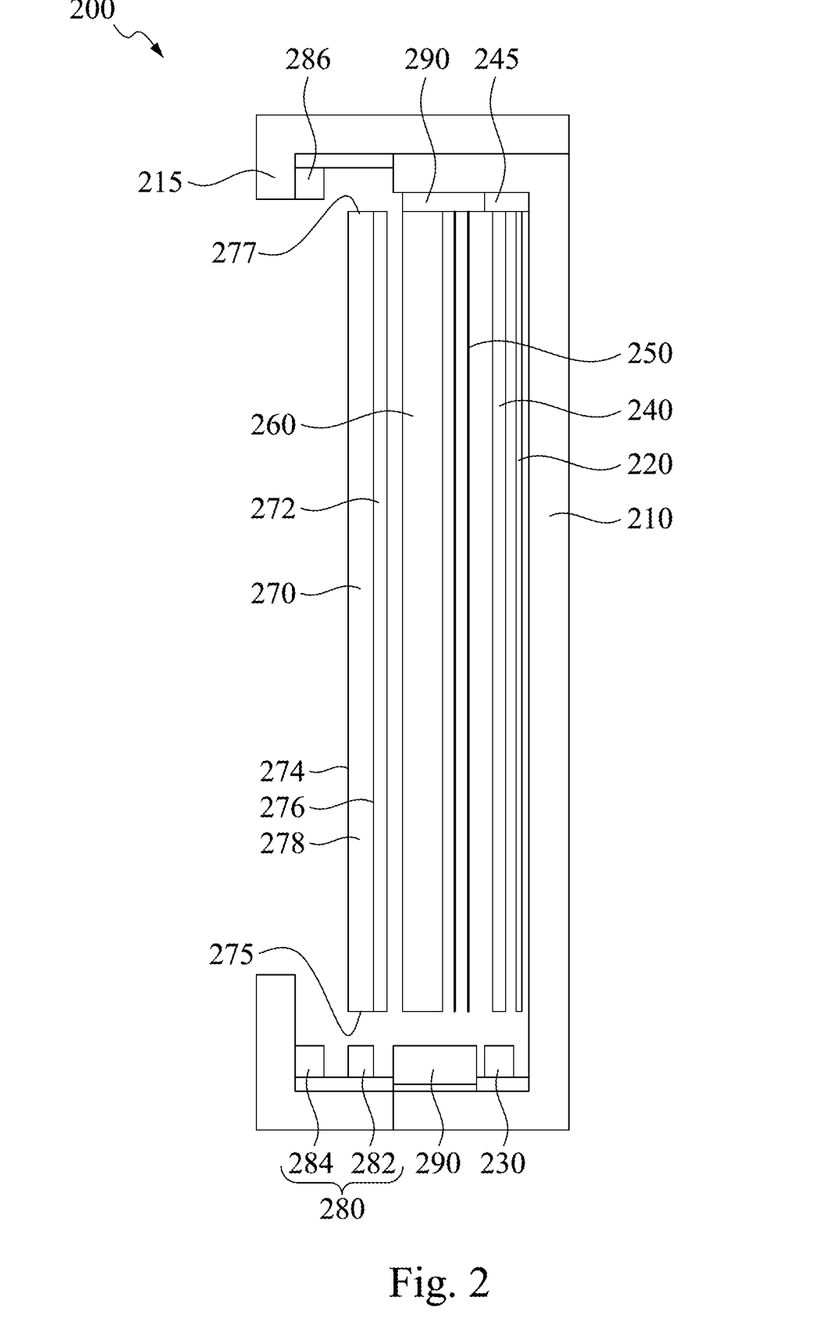
FIG. 2 illustrates a schematic diagram showing an ultraviolet sterilization display device according to another embodiment of the present invention.
Figure 3:
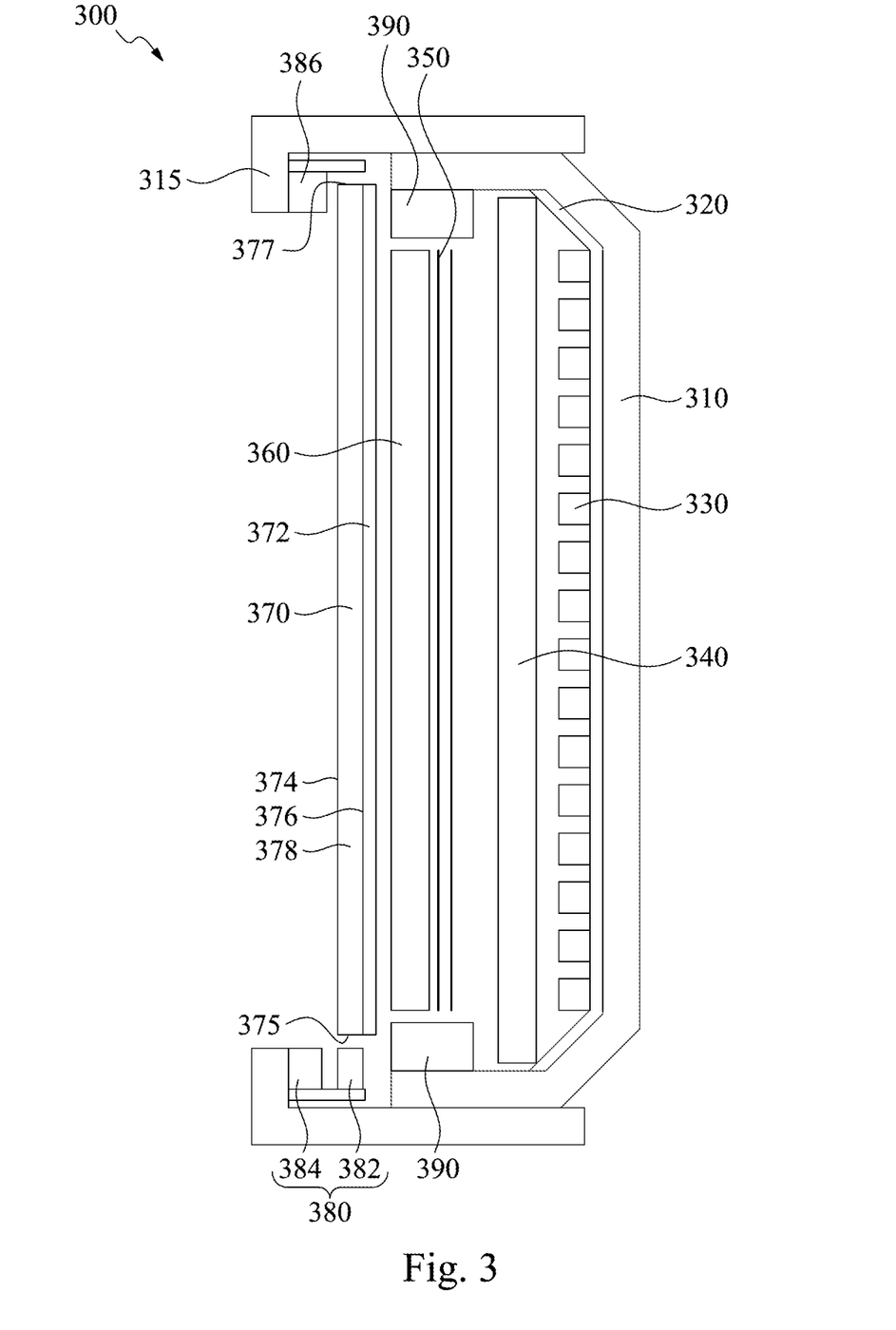
FIG. 3 illustrates a schematic diagram showing an ultraviolet sterilization display device according to further another embodiment of the present invention.
Figure 4:
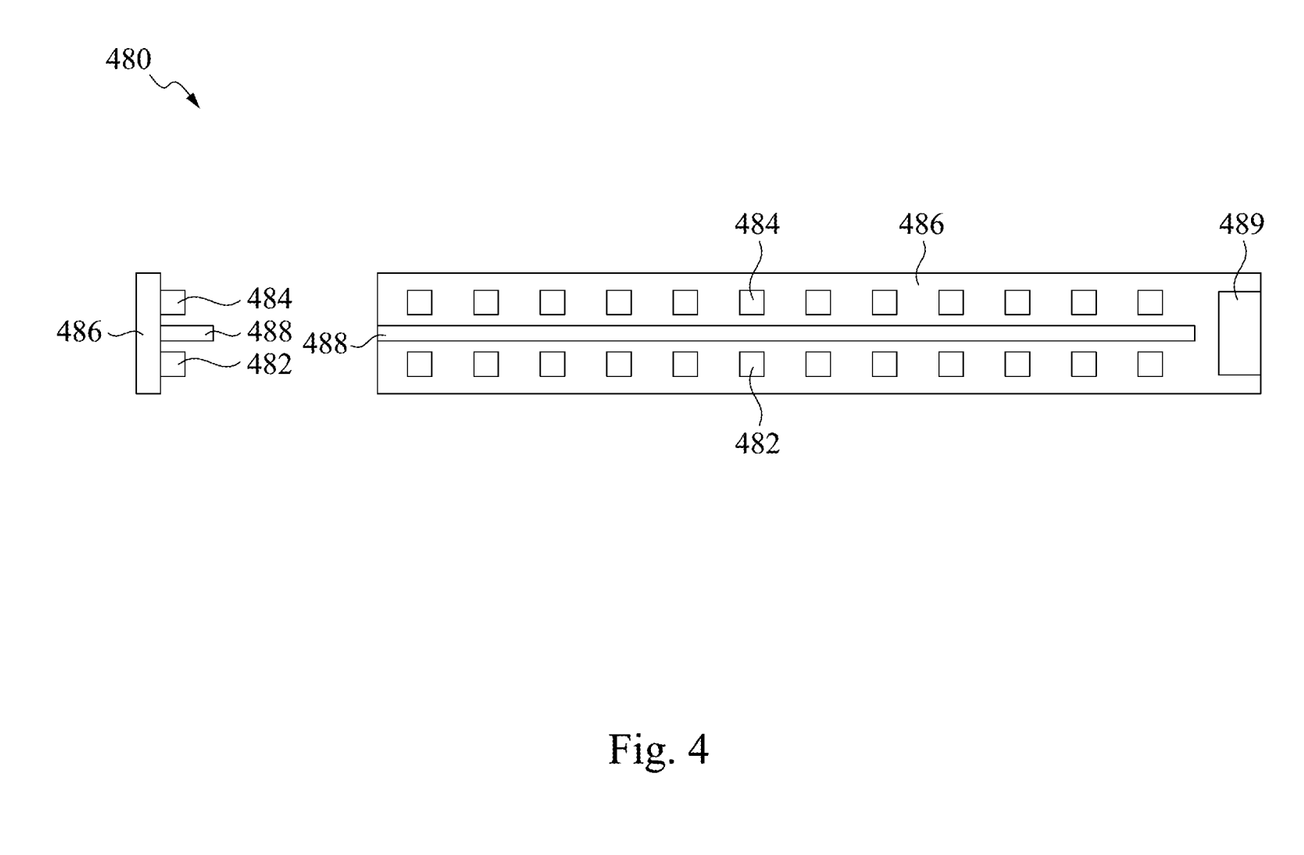
FIG. 4 illustrates a schematic diagram showing a light emitting diode module of the ultraviolet sterilization display device according to embodiments of the present invention.
Figure 5:
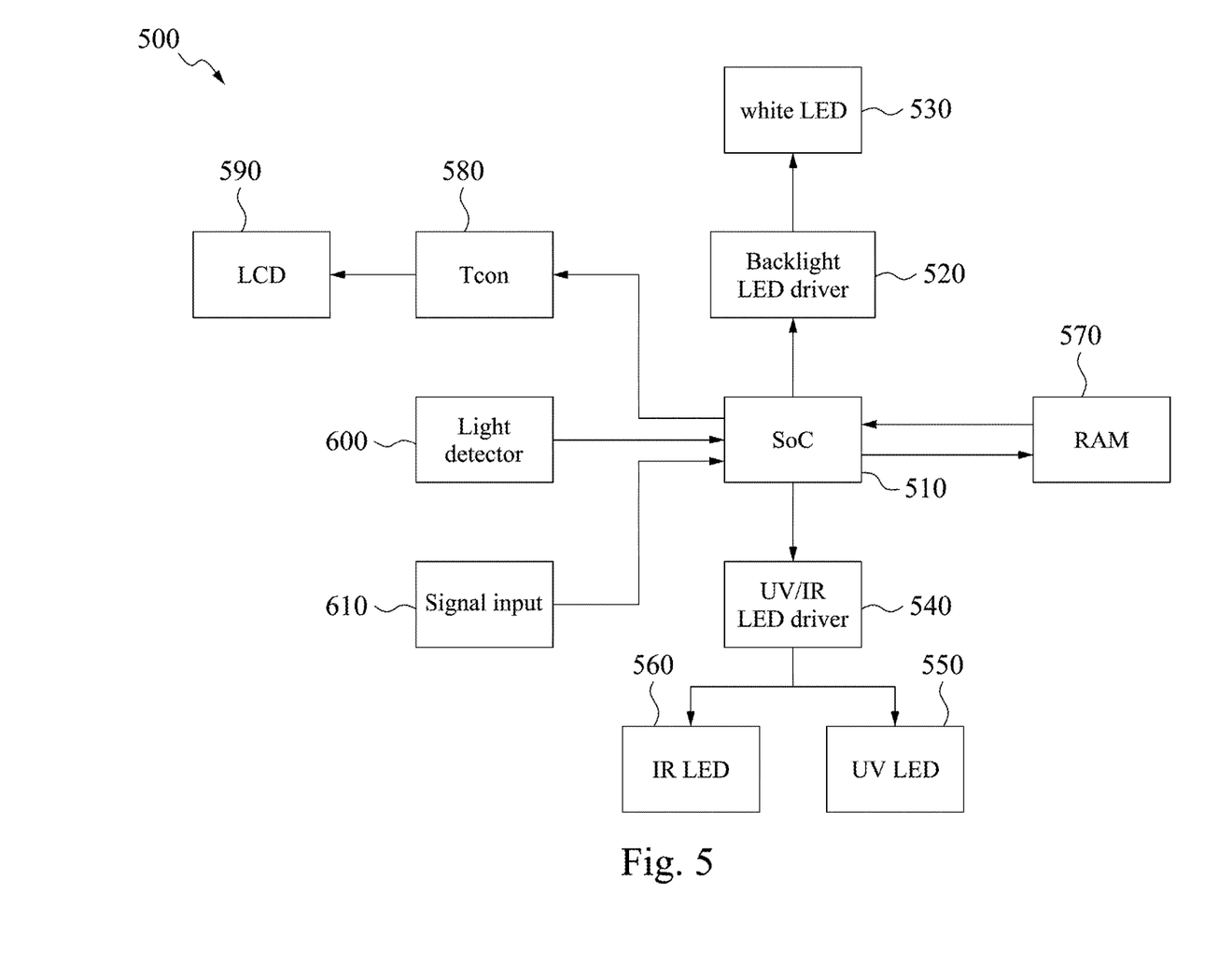
FIG. 5 illustrates a system block diagram of the ultraviolet sterilization display device according to embodiments of the present invention.

FIGS. 1, 2 and 3 illustrate the ultraviolet sterilization display device according to embodiments of the present invention, FIG. 4 illustrates a light emitting diode module of the ultraviolet sterilization display device according to embodiments of the present invention, and FIG. 5 illustrates a system block diagram thereof.

FIG. 1 illustrates a thin touch-control display device as an example. The thin touch-control display device with ultraviolet sterilization function can be a mobile communication device, such as a mobile phone or a tablet computer. In some embodiments, the thin touch-control display device can be a large display device. The ultraviolet sterilization display device 100 in FIG. 1 includes a back plate 110, a reflector 120, a backlight source 130, a light guide film 140, a plurality of optical films 150, a liquid crystal display panel 160 and a sterilization panel 170.

The reflector 120 is fixed to the back plate 110, the light guide film 140 is disposed on the reflector 120, the plurality of optical films 150 are disposed on the light guide film 140, and the liquid crystal display panel 160 is disposed on the optical film 150. The sterilization panel 170 is disposed on the liquid crystal display panel 160 and fixed to the back plate 110. In addition, the backlight source 130, e.g. a plurality of white light emitting diodes, is also fixed inside the back plate 110 and aligns with the one side of the light guide film 140.

The sterilization panel 170 includes an inner surface 176, an outer surface 174, a light incident surface 175, an end surface 177 and two side surfaces 178. The light incident surface 175, the end surface 177 and the side surfaces 178 are formed between the inner surface 176 and the outer surface 174. The light emitting diode module 180 includes a plurality of UV light emitting diodes aligning with the light incident surface 175 of the sterilization panel 170. In addition, the optical film 150 and the liquid crystal display panel 160 are fixed to the frame 190. In some embodiments, the back plate 110 of the touch-control display device is an assembly of a plurality of casing structures. For example, the side frame is not integrally formed with the back plate 110 but fixed to the back plate 110 by fasteners. The backlight source 130, the light emitting diode module 180 and the frame 190 can be placed on an inner side of the side frame or the back plate 110, or be on different sides of the side frame or the back plate. In some embodiments, the frame 190 can be integrally formed with the side frame. The derivative designs or changes do not depart from the spirit and the scope of the invention.

It is worth noting that a titanium dioxide thin film 172 is disposed or formed on the inner surface 176 of the sterilization panel 170 to prevent the liquid crystal display panel 160, the electronic parts or the optical films behind the sterilization panel 170 from being irradiated by the ultraviolet (UV) light emitted by the ultraviolet light emitting diodes, so the degradation caused by the UV light can be avoided. In some embodiments, the thickness of the titanium dioxide thin film 172 is about 100 micrometers or less.

The UV light emitting diode, for example, can be the UV-C light emitting diode with emission wavelengths in the range of 200 to 280 nm, which can generate short wavelength UV light that is utilized to sterilize the sterilization panel 170. However, although the UV-C light can provide a better bactericidal effect, part of the emitted UV light may cause damages to human cells. Optical materials, for example, plastics, may also be vulnerable to the UV light which will cause yellowing, accelerated aging and cracking. Therefore, the titanium dioxide thin film 172 is disposed or formed on the inner surface 176 of the sterilization panel 170 in order to absorb the UV light according to some embodiments of the present disclosure, such that the accelerated aging of the internal electronic parts and the optical materials caused by the UV light can be prevented. In addition, the thin touch-control display device according to some embodiments of the present disclosure only activates panel sterilization when the thin touch-control display device is not operated by the users. For example, the system of the touch-control display device automatically initiates the ultraviolet sterilization process when the touch-control display device is not operated by any user for a predetermined time period, or when the touch-control display device is in a standby state or a shutdown state. In some embodiments, the touch-control display device may notify the user not to operate by displaying a picture on the screen, turning on an indicator light on the case, playing sound from the speaker, or starting vibration of the touch-control display device when the touch-control display device is going to initiate the ultraviolet sterilization function or is executing the ultraviolet sterilization function. In some embodiments, the touch-control display device initiates the sterilization function when the touch-control display device is not operated by any user and an ambient light sensor on the side surface of the touch-control display device detects that the ambient light brightness is lower than a predetermined brightness for a period of time. In some embodiments, the user can sterilize the surface of an object by moving the handheld touch-control display device close to the object and facing the sterilization panel to the close object during execution of the ultraviolet light sterilization function. The user can turn off or on the ultraviolet light sterilization through the button or combination of buttons on the handheld touch-control display device which acts as a handheld sterilization device.

In some embodiments, the ultraviolet sterilization process of the touch-control display device includes notifying not to operate the touch-control display device by displaying a warning picture, turning on an indicator light, playing warning sound, or starting vibration of the touch-control display device when the touch-control display device is going to initiate the ultraviolet sterilization process or is executing the ultraviolet sterilization process.

In some embodiments, the sterilization panel 170 is a light guide plate made of UV resistant material, and preferably the light transmittance of the light guide plate made of UV resistant material is greater than 80%.

In some embodiments, the light guide plate made of UV resistant material is a glass panel, such as a tempered glass panel.

In some embodiments, the glass panel is a high light transmission glass substrate plate made of glass materials, such as borosilicate glass or aluminosilicate glass.

In some embodiments, a vacuum deposition process is performed on the glass substrate, such as physical vapor deposition, to coat a layer of titanium dioxide thin film.

Therefore, the titanium dioxide thin film can provide more than 90% absorption rate for light with wavelengths below 350 nanometers (nm) during the ultraviolet sterilization, and most of the ultraviolet light will not penetrate through the glass substrate and affect the electronic parts and optical materials behind the glass substrate. In addition, the wavelength of the light emitted by the light source of the backlight module is generally above 425 nanometers and the titanium dioxide thin film does not affect the penetration of such light emitted by the light source of the backlight module. Therefore, the titanium dioxide thin film can protect the lifespan of the components of the display apparatus during the UV sterilization, and the brightness and picture quality of the display apparatus are not affected by the titanium dioxide thin film.

In some embodiments, the titanium dioxide thin film can effectively absorb the UV light emitted by the UV light emitting diode during the UV germicidal irradiation and protect the components vulnerable to UV light, such as the polarizer, the optical films, the light guide plate, or the diffuser in the backlight module.

In some embodiments, the end surface 177 of the sterilization panel 170 is opposite to the light incident surface 175 of the sterilization panel 170, and the two side surfaces 178 connect the light incident surface 175 and the end surface 177, wherein the end surface 177 and the side surfaces 178 include a reflecting layer. For example, a U-shaped reflecting layer is formed surrounding the end surface 177 and the two side surfaces 178 of the sterilization panel 170.

In some embodiments, the reflecting layer includes a white reflecting surface or a silver reflecting surface to reflect the UV light, which can improve the utilization efficiency of UV light and protect the electronic components and materials around the sterilization panel 170.

FIG. 2 illustrates an edge-lit type touch-control display device with UV sterilization and IR proximity detection function as an example. The ultraviolet sterilization display device 200 includes a back plate 210, a reflector 220, a backlight source 230, a light guide plate 240, a plurality of optical films 250, a liquid crystal display panel 260, and a sterilization panel 270.

The reflector 220 is fixed to the back plate 210, the light guide plate 240 is disposed on the reflector 220, and a plurality of optical films 250 are disposed on the light guide plate 240. The liquid crystal display panel 260 is fixed to the frame 290, and the optical films 250 are disposed on the inner surface of the liquid crystal display panel 260. The sterilization panel 270 is disposed on the outer surface of the liquid crystal display panel 260, and is fixed to the bezel 215. In addition, the backlight source 230, for example, a plurality of white light emitting diodes, is also fixed to the back plate 210 and aligns with one end surface of the light guide plate 240. The other end surface of the light guide plate 240 abuts against the silicon rubber 245.

The sterilization panel 270 includes an inner surface 276, an outer surface 274, a light incident surface 275, an end surface 277 and two side surfaces 278. The light incident surface 275, the end surface 277 and the side surfaces 278 are formed between the inner surface 276 and the outer surface 274.

The light emitting diode module 280 includes a plurality of UV light emitting diodes 282, a plurality of infrared (IR) light emitting diodes 284, and a plurality of light detectors 286 for detecting the infrared light emitted from the IR light emitting diodes 284, which are utilized to determine whether the touch screen needs to be sterilized. The UV light emitting diodes 282 are aligned with the light incident surface 275 of the sterilization panel 270, and the IR light emitting diodes 284 are disposed adjacent to the outer surface 274 of the sterilization panel 270 and emit the infrared rays to the light detectors 286 at the other end of the sterilization panel 270. If any of the infrared rays is blocked by an object and cannot reach the light detectors 286, it is determined that the sterilization panel 270 is contacted by the object and needs to be sterilized. In some embodiments, the IR light emitting diodes 284 and the UV light emitting diodes 282 are all fixed adjacent to the light incident surface 275 of the sterilization panel 270, and the light detectors 286 are fixed adjacent to the end surface 277 of the sterilization panel 270.

In some embodiments, the light emitting diode module 280 is incorporated in a 55 inch or larger touch-control screen device. The light emitting diode module 280 can provide ultraviolet rays to sterilize the touch screen and the infrared rays to detect whether the touch screen is contacted by the user and needs to be sterilized. In some embodiments, the infrared light emitting diodes 284 and the light detectors 286 can be replaced with other types sensors to determine whether the touch screen is contacted or approached by an object, such as sound wave sensors or electromagnetic signal sensors which can detect whether the sound wave or the electromagnetic signals are blocked or reflected by an object, or proximity sensors which detect heat or other types signals from a nearby object.

Similarly, a titanium dioxide thin film 272 is disposed or formed on the inner surface 276 of the sterilization panel 270, which can prevent the liquid crystal display panel 260, electronic parts and optical components from aging caused by the UV light irradiation emitted by the UV light emitting diodes. In some embodiments, the thickness of the titanium dioxide thin film 272 is 100 micrometers or less.

The UV light emitting diode, for example, can be the UV-C light emitting diode with UV-C light emission wavelength. The sterilization panel 270 is also a light guide plate made of UV resistant material. Preferably, the light guide plate is formed from the UV resistant material with a light transmittance greater than 80%, which can be, for example, a glass panel, a tempered glass panel, and a high light transmission panel made of borosilicate glass or aluminosilicate glass.

The titanium dioxide thin film disposed or formed on the sterilization panel 270 can effectively absorb the UV light emitted by the UV light emitting diode during UV germicidal irradiation and protect the components vulnerable to UV light, such as polarizer, the optical films, the light guide plate, the diffuser or other internal parts in the backlight module.

In some embodiments, the end surface 277 and the side surfaces 278 of the sterilization panel 270 include a reflecting layer, such as a U-shaped reflecting layer surrounding the end surface 277 and the two side surfaces 278 of the sterilization panel 270. The reflecting layer can include a white reflecting surface or a silver reflecting surface to reflect the UV light, which can improve the utilization efficiency of the UV light and protect the electronic components and materials around the sterilization panel 270.

FIG. 3 illustrates a direct-lit touch-control display device with UV sterilization and IR proximity detection function as an example. The ultraviolet sterilization display device 300 includes a back plate 310 and a reflector 320, a backlight source 330, a diffuser 340, a plurality of optical films 350, a liquid crystal display panel 360, and a sterilization panel 370.

The reflector 320 is fixed to the back plate 310, the diffuser 340 is disposed on the reflector 320, and a plurality of optical films 350 are disposed on the diffuser 340. The liquid crystal display panel 360 is disposed on the optical film 350. The sterilization panel 370 is disposed on the liquid crystal display panel 360 and fixed to the bezel 315. The liquid crystal display panel 360 is fixed to the frame 390, and the optical films 350 are disposed on the inner surface of the liquid crystal display panel 360. In addition, the backlight source 330, e.g. a plurality of white light emitting diodes, is disposed on the back plate 310 between the reflector 320 and the diffuser 340.

The sterilization panel 370 includes an inner surface 376, an outer surface 374, a light incident surface 375, an end surface 377 and two side surfaces 378. The light incident surface 375, the end surface 377 and the side surfaces 378 are formed between the inner surface 376 and the outer surface 374.

The light emitting diode module 380 includes a plurality of UV light emitting diodes 382, a plurality of infrared (IR) light emitting diodes 384, and a plurality of light detectors 386 for detecting the infrared light emitted from the IR light emitting diodes 384, which are utilized to determine whether the touch screen needs to be sterilized. The UV light emitting diodes 382 are aligned with the light incident surface 375 of the sterilization panel 370, and the IR light emitting diodes 384 are disposed adjacent to the outer surface 374 of the sterilization panel 370 and emit the infrared rays to the light detectors 386 at the other end of the sterilization panel 370. If any of the infrared rays is blocked by an object and cannot reach the light detectors 286, it is determined that the sterilization panel 370 is contacted by the object and needs to be sterilized. In some embodiments, the IR light emitting diodes 384 and the UV light emitting diodes 382 are all fixed adjacent to the light incident surface 375 of the sterilization panel 370, and the light detectors 386 are fixed adjacent to the end surface 377 of the sterilization panel 370.

In some embodiments, the light emitting diode module 380 is incorporated in a 55 inches or larger touch-control screen device. The light emitting diode module 380 can provide the ultraviolet rays to sterilize the touch screen and the infrared rays to detect whether the touch screen is contacted by the user and needs to be sterilized. In some embodiments, the infrared light emitting diodes 384 and the light detectors 386 can be replaced with other types sensors to determine whether the touch screen is contacted or approached by an object, such as sound wave sensors or electromagnetic signal sensors which can detect whether the sound wave or electromagnetic signals are blocked or reflected by an object, or proximity sensors which can detect heat or other types signals from a nearby object.

Similarly, a titanium dioxide thin film 372 is disposed or formed on the inner surface 376 of the sterilization panel 370, which can prevent the liquid crystal display panel 260, electronic parts and optical components from aging caused by the UV light irradiation emitted by the UV light emitting diodes. In some embodiments, the thickness of the titanium dioxide thin film 372 is 100 micrometers or less.

The UV light emitting diode, for example, can be the UV-C light emitting diode with UV-C light emission wavelength. The sterilization panel 370 is also a light guide plate made of UV resistant material. Preferably, the light guide plate is formed by the UV resistant material with a light transmittance greater than 80%, which can be, for example, a glass panel, a tempered glass panel, and a high light transmission panel made of the borosilicate glass or aluminosilicate glass.

The titanium dioxide thin film disposed or formed on the sterilization panel 370 can effectively absorb the UV light emitted by the UV light emitting diode during UV germicidal irradiation and protect components vulnerable to UV light, such as the polarizer, the optical films, the light guide plate, the diffuser or other internal parts in the backlight module.

In some embodiments, the end surface 377 and the side surfaces 378 of the sterilization panel 370 include a reflecting layer, such as a U-shaped reflecting layer surrounding the end surface 377 and the two side surfaces 378 of the sterilization panel 370. The reflecting layer can include a white reflecting surface or a silver reflecting surface to reflect the UV light, which can improve the utilization efficiency of the UV light and protect the electronic components and materials around the sterilization panel 370.

Referring to FIG. 4, in some embodiments, the light emitting diode module 480 includes a plurality of UV light emitting diodes 482, a circuit board 486 and a plurality of IR light emitting diodes 484 or any suitable sensors. The UV light emitting diode 282, the IR light emitting diodes 484 or any suitable sensors are fixed on the circuit board 486.

In some embodiments, the light emitting diode module 480 further includes a separator 488 disposed between the UV light emitting diodes 482 and the IR light emitting diodes 484 or suitable sensors which blocks and reflects the UV rays emitted by the UV light emitting diodes 482 and prevents the IR light emitting diodes 484 or suitable sensors from damages caused by UV irradiation. In addition, the circuit board 486 of the light emitting diode module 480 further includes a connector 489 which electrically connects to the control circuit of the ultraviolet sterilization display device, which can be, for example, a controller chip, a system on chip (SoC) and/or a LED driver.

Referring to FIG. 5, a system block diagram of an ultraviolet sterilization display device 500 is illustrated. As shown in FIG. 5, the control chip 510 of the ultraviolet sterilization display device provide control information to the backlight LED driver 520 to drive the white light emitting diode 530. At the same time, the control chip 510 estimates the phase delay time in accordance with the turn-on time of the liquid crystal display 590, and provide timing information to the timing controller 580 that turns on the liquid crystal display 590 synchronously.

The proximity sensor of the ultraviolet sterilization display device 500 is activated when the liquid crystal display 590 is displaying a picture. Taking the IR light emitting diode 560 and the light detector 600 as an example of the proximity sensor, the IR light emitting diode 560 outputs the infrared light which should be received by the light detector 600 if there is no object contacting the touch screen, and the control chip 510 determines whether the touch screen is contacted according to the detection signals of the light detector 600. The UV light emitting diode 550 is still turned off and the UV/IR driver 540 does not drive the UV light emitting diode 550 when there is an object contacting the touch screen. Therefore, the UV light emitting diode 550 does not emit ultraviolet rays which may influence the user's interactions with the touch screen. After the user stops using the touch screen, the user can manually activate the ultraviolet sterilization by selecting the activation option in the on-screen display (OSD) menus of the ultraviolet sterilization display device. The control chip 510 will output an activate signal to the UV/IR driver 540 which drives the UV light emitting diode 550 to irradiate the UV lights to touch screen for sterilization. In some embodiments, the display device can also be designed to include user input component, such as button, key, keyboard, trackball or other control components placed at the position other than the touch screen, which allows the users to activate the UV sterilization process or operate the on screen display menus through the user input devices. The user can also use an external device to transmit a control signal to the display device through the input port 610 or wireless network interface, which controls the display device and activate the UV sterilization process.

In some embodiments, the display device, for example, a thin touch-control display device or a small mobile display device, includes a proximity sensor to detect whether the user is operating the display device. The ultraviolet sterilization process will only be activated when the proximity sensor detects that the display device is not used by any user. If an object is detected close to the touch screen during sterilization, the UV sterilization process will be interrupted immediately. In some embodiments, the display device is a thin touch-control display device or a small mobile display device, wherein the touch-control signals generated by the touch screen or the ambient brightness signals generated by the ambient light sensor can be utilized to determine whether the touch screen is used by the user. By this way, the system of the display device can decide whether to activate the sterilization process at any time, the UV sterilization process can be interrupted and the UV light can be turned off immediately while the user begins to use the touch screen.

The information of sterilizing common pathogens, such as bacteria or viruses, is stored in the memory component 570. For example, the UV irradiation time for sterilizing common *Escherichia coli* may be about 20 seconds and sterilizing *Salmonella* may be about 60 seconds.

In some embodiments, the display device automatically determines whether to activate the sterilization process at any time, wherein the control chip 510 automatically turns on the UV light emitting diode 550 after the system of the display device is in shutdown or standby states. When the system is in shut down or standby states, the control chip 510 automatically outputs an activation signal to the UV/IR driver 540 which drives the UV light emitting diode 550, so the touch screen will be sterilized or disinfected by ultraviolet radiation. In some embodiments, the UV/IR driver 540 simultaneously drives the IR light emitting diode 560 to emit infrared rays during the sterilization process, and the light detector 600 is also activated to receive infrared rays concurrently. The infrared rays are used to detect whether there is an object approaching the liquid crystal display 590 during sterilization, such as a hand. If an object is detected approaching the liquid crystal display 590, the power supplied to the UV light emitting diode will be turned off or a deactivation signal will be output to the UV/IR driver 540 to stop driving the UV light emitting diode 550, so the emission of ultraviolet rays will be stopped and the safety of the user can be ensured. Similarly, in some embodiments, when the user manually activates the UV sterilization process through the OSD menus, the UV/IR driver 540 will drive the IR light emitting diode 560 to emit infrared rays and the light detector 600 will simultaneously start to receive infrared rays. If the system detects an object approaching to touch the liquid crystal display 590, the current supplied to the UV light emitting diode 550 will be cut off or a deactivation signal will be outputted to the UV/IR driver 540 in order to stop driving the UV light emitting diode 550 to emit ultraviolet rays, so the safety of the user can be ensured. In some embodiments, the IR light emitting diode 560 and the light detector 600 can be replaced with other types of proximity sensors which can detect whether there is an object or human body approaching the liquid crystal display 590.

In some embodiments, the control chip 510 stores the detection records from the proximity sensor in the memory component 570, such as the records of the light detector 600 receiving the infrared rays from the IR light emitting diode 560, which includes the number of times and the duration that the infrared rays are blocked. Such records are utilized to determine whether there is an object close to contact the touch screen and count the cumulative time to determine whether to activate the sterilization process. For example, when the system is in shut down or standby states, the control chip 510 determines that there is no need to activate the UV sterilization process if there is no record that the touch screen has been contacted. In some embodiments, the control chip 510 determines whether to activate the UV sterilization process based on the calculated cumulative time that the touch screen has been contacted by any object. The cumulative time is calculated based on the detection records stored in the memory component 570. For example, the longer cumulative time that the touch screen has been contacted, the longer time period of the UV sterilization process will be set to perform during the shutdown or standby duration of the system by the control chip 510. Alternatively, the control chip 510 can determine to adjust the setting of time period for next UV sterilization process if the cumulative time that the touch screen has been contacted exceeds the threshold. For example, the time period of the next UV sterilization process is extended longer if the calculated cumulative time exceeds the longer threshold time period. In some embodiments, the control chip 510 resets the cumulative time and the detection records in the memory component 570 or move the detection records to archive as historical data after the system completes the UV sterilization process, so the determinations will not be affected by the expired or outdated records.

Accordingly, the present invention discloses a display device with ultraviolet sterilization function, wherein most of the emitted ultraviolet rays are totally reflected in the glass panel and leave from the outer surface without titanium dioxide coated, so the pathogens, such as bacteria and viruses, on the outer surface of the glass panel will be disinfected or sterilized by the ultraviolet rays. In addition, the UV-C rays are short-wavelength light with very short transmission distance, so the UV-C rays will not cause harms to any objects at longer than short distance. Furthermore, the display device with ultraviolet sterilization function cuts off the power supplied to the UV light emitting diodes when the IR light emitting diodes/IR light detectors detect that the outer surface of the glass panel is contacted by a user-thereby the safety of the display device with UV sterilization function during the UV sterilization process is effectively improved.

As is understood by a person skilled in the art, the foregoing preferred embodiments of the present invention are illustrative of the present invention rather than limiting of the present invention. It is intended that various modifications and similar arrangements be included within the spirit and scope of the appended claims, the scope of which should be accorded the broadest interpretation so as to encompass all such modifications and similar structures.

What is claimed is:

1. An ultraviolet sterilization display device, comprising:
   a sterilization panel having an inner surface, an outer surface and a light incident surface;
   a titanium dioxide thin film disposed or formed on the inner surface of the sterilization panel;
   a light emitting diode module aligning with the light incident surface of the sterilization panel, wherein the light emitting diode module comprises a plurality of ultraviolet light emitting diodes;
   a control chip generating a signal to activate the ultraviolet light emitting diodes to emit ultraviolet lights for a period of time, wherein the control chip stores detection records comprising a number of times and duration of an object close to the sterilization panel into a memory component; and
   a display panel adjacent to the inner surface of the sterilization panel, wherein the sterilization panel further comprises an end surface opposite to the light incident surface, and two side surfaces connected to the light incident surface and the end surface, and the end surface and the side surfaces comprises a reflecting layer.

2. The ultraviolet sterilization display device of claim 1, wherein the reflecting layer includes a white surface or a silver surface.

3. The ultraviolet sterilization display device of claim 1, wherein the sterilization panel is a light guide plate formed by a UV resistant material having a non-ultraviolet light transmittance greater than 80%.

4. The ultraviolet sterilization display device of claim 1, wherein the light emitting diode module further comprises:
   a circuit board fixing the ultraviolet light emitting diodes;
   a plurality of infrared light emitting diodes fixed on the circuit board; and
   a plurality of light detectors detecting lights of the infrared light emitting diodes.

5. The ultraviolet sterilization display device of claim 1, further comprising a proximity sensor to detect the object close to the sterilization panel.

6. An ultraviolet sterilization display device, comprising:
   a sterilization panel having an inner surface, an outer surface and a light incident surface;
   a titanium dioxide thin film disposed or formed on the inner surface of the sterilization panel;
   a light emitting diode module aligning with the light incident surface of the sterilization panel, wherein the light emitting diode module comprises a plurality of ultraviolet light emitting diodes;
   a display panel adjacent to the inner surface of the sterilization panel;
   a proximity sensor detecting whether an object is close to the sterilization panel or contacting the sterilization panel;
   a memory component storing detection records of the proximity sensor; and
   a control chip generating a signal to activate the ultraviolet light emitting diodes to emit ultraviolet lights for a period of time when the ultraviolet sterilization display device is in a shutdown state or a standby state and the stored detection records include that the object was detected as close to the sterilization panel or contacting the sterilization panel,
   wherein the stored detection records in the memory component is reset after the ultraviolet light emitting diodes are driven to emit ultraviolet lights for the period of time, wherein the sterilization panel further comprises an end surface opposite to the light incident surface, and two side surfaces connected to the light incident surface and the end surface, and the end surface and the side surfaces comprises a reflecting layer, wherein the stored detection records comprise a number of times and duration of the object close to the sterilization panel.

7. The ultraviolet sterilization display device of claim 6, wherein the control chip generates the signal to activate the ultraviolet light emitting diodes are determined according to the number of times and duration of the object close to the sterilization panel.

8. The ultraviolet sterilization display device of claim 6, wherein the control chip further turns off the ultraviolet light emitting diodes when the proximity sensor detects an object is close to the sterilization panel.

9. The ultraviolet sterilization display device of claim 6, wherein the reflecting layer includes a white surface or a silver surface.

10. The ultraviolet sterilization display device of claim 6, wherein the sterilization panel is a light guide plate formed by a UV resistant material having a non-ultraviolet light transmittance greater than 80%.

11. An ultraviolet sterilization touch-control display device, comprising:
   a sterilization panel having an inner surface, an outer surface and a light incident surface;
   a titanium dioxide thin film disposed or formed on the inner surface of the sterilization panel;
   a light emitting diode module aligning with the light incident surface of the sterilization panel, wherein the light emitting diode module comprises a plurality of ultraviolet light emitting diodes;
   a display panel adjacent to the inner surface of the sterilization panel; and
   a control chip automatically generating a signal to activate the ultraviolet light emitting diodes to emit ultraviolet lights for a period of time when the ultraviolet sterilization touch-control display device is not operated for a predetermined time period, or when the ultraviolet sterilization touch-control display device is in a standby state or a shutdown state, wherein the sterilization panel further comprises an end surface opposite to the light incident surface, and two side surfaces connected to the light incident surface and the end surface, and the end surface and the side surfaces comprises a reflecting layer, wherein the ultraviolet sterilization touch-control display device automatically initiates a sterilization process when the ultraviolet sterilization touch-control display device is not operated and an ambient light sensor on a side surface of the ultraviolet sterilization touch-control display device detects that ambient light brightness is lower than a predetermined brightness value for the period of time.

12. The ultraviolet sterilization touch-control display device of claim 11, wherein the ultraviolet sterilization touch-control display device notifies not to operate the ultraviolet sterilization touch-control display device by displaying a warning picture, turning on an indicator light, playing warning sound, or starting vibration of the ultraviolet sterilization touch-control display device when the ultraviolet sterilization touch-control display device is going to initiate the sterilization process or is executing the sterilization process.

13. The ultraviolet sterilization touch-control display device of claim 11, further comprising:
   a proximity sensor detecting whether an object is contacting the sterilization panel or a touch-control signal is generated; and
   a memory component storing detection record to form stored detection records;
   wherein the control chip automatically generates the signal to activate the ultraviolet light emitting diodes to emit ultraviolet lights for the period of time when the ultraviolet sterilization touch-control display device is in the shutdown state or the standby state and the stored detection records include that the object was detected as close to the sterilization panel or contacting the sterilization panel or the touch-control signal was generated.

14. The ultraviolet sterilization touch-control display device of claim 11, wherein the reflecting layer includes a white surface or a silver surface.

15. The ultraviolet sterilization touch-control display device of claim 11, wherein the sterilization panel is a light guide plate formed by a UV resistant material having a non-ultraviolet light transmittance greater than 80%.

* * * * *